(12) United States Patent
Syage et al.

(10) Patent No.: US 7,401,498 B2
(45) Date of Patent: Jul. 22, 2008

(54) MULTIPLE TRACE PORTAL DETECTION SYSTEMS

(75) Inventors: Jack A. Syage, Huntington Beach, CA (US); Karl A. Hanold, Huntington Beach, CA (US)

(73) Assignee: Syagen Technology, Tustin, CA (US)

( * ) Notice: Subject to any disclaimer, the term of this patent is extended or adjusted under 35 U.S.C. 154(b) by 0 days.

(21) Appl. No.: 11/075,199

(22) Filed: Mar. 7, 2005

(65) Prior Publication Data

US 2006/0196249 A1     Sep. 7, 2006

(51) Int. Cl.
*G01N 30/00* (2006.01)
*G01N 1/14* (2006.01)

(52) U.S. Cl. ............. 73/28.01; 73/863.21; 73/863.33; 73/864.33

(58) Field of Classification Search ............. 73/28.01, 73/863.21, 863.33, 864.33
See application file for complete search history.

(56) References Cited

U.S. PATENT DOCUMENTS

| | | | | |
|---|---|---|---|---|
| 4,987,767 A | * | 1/1991 | Corrigan et al. | 73/23.36 |
| 5,162,652 A | * | 11/1992 | Cohen et al. | 250/288 |
| 5,915,268 A | * | 6/1999 | Linker et al. | 73/23.2 |

* cited by examiner

*Primary Examiner*—Daniel S Larkin
(74) *Attorney, Agent, or Firm*—Ben J. Yorks; Irell & Manella LLP

(57) ABSTRACT

A detector system that can analyze multiple samples with a single detector. The detector may contain a portal with a first opening and a second opening. A first sample is obtained from the first opening and a second sample is obtained from the second opening. The openings are coupled to a single detector that can analyze both samples.

13 Claims, 8 Drawing Sheets

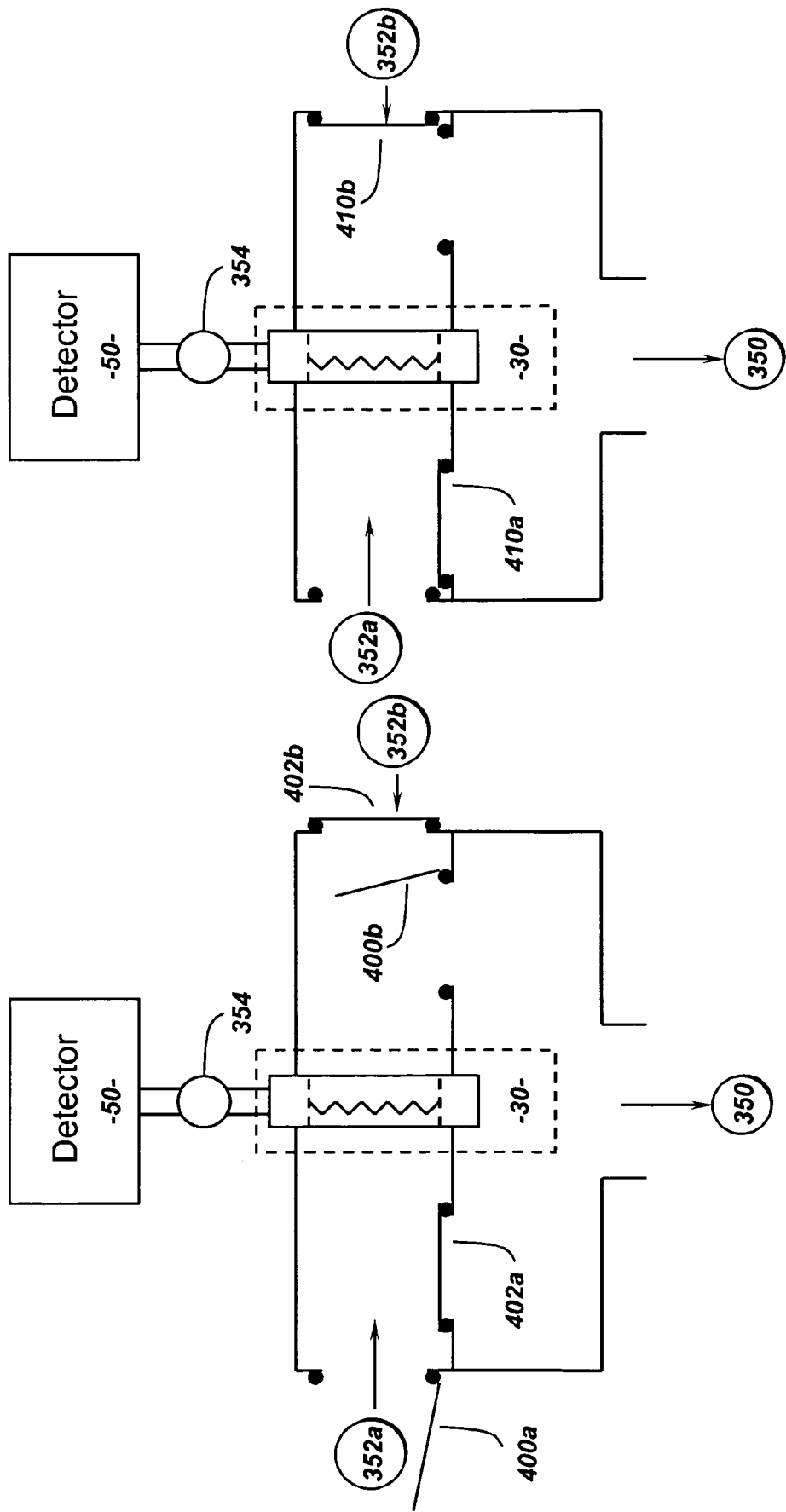

MULTIPLE TRACE PORTAL DETECTION SYSTEMS

BACKGROUND OF THE INVENTION

1. Field of the Invention

The present invention relates to the field of detection apparatus used to screen individuals for the presence of explosives and other chemical entities.

2. Background Information

The growing concern over security in public venues has led to development of new technologies capable of rapidly detecting the presence of illicit and hazardous materials. One of the lead organizations in this effort is the Transportation Security Agency (TSA), who is responsible for ensuring safety of air travel and has invested significantly in developing technologies to combat the potential for attacks by explosive devices.

Two types of detectors are used for screening baggage and people. Explosive detection systems (EDSs) detect bulk explosives hidden in checked baggage and frequently operate using dual x-ray tomography. Explosives trace detectors (ETDs) detect vapor or particles of explosives that are contaminated on people and the surface of baggage. ETDs are also used to resolve alarms from EDSs. Currently ETDs are used on a selective basis to screen for personal items and carry-on bags, but not for directly screening individuals. The lack of a capability to screen for explosives hidden on an individual is arguably the greatest vulnerability in aviation security. Though most of the attention for explosives threat detection is focused on aviation security, in fact security is an issue for many venues including other types of transportation, buildings, ports, stadiums, military base and field operations, and in general any high traffic environment.

Several portal concepts using ETDs have been developed and tested. The most promising are based on non-intrusive (non-contact) removal of particles from clothing, followed by high-flow collection of the particles on the surface of a mesh or substrate, and then thermal desorption into an ETD. For examples Linker et al. disclosed in U.S. Pat. No. 5,915,268 a portal device that uses air jets to dislodge particles from a person and a downward flow of air to entrain and carry the particles to a concentrator device. Another portal method was disclosed by Settles in U.S. Pat. No. 6,073,499, which involves a passive method of particle collection relying on the upward flow of air around people due to thermal conductivity in what is called the human thermal plume (HTP). Jenkins et al disclosed in U.S. Pat. No. 6,708,572 a similar method that uses air jets to assist the upward flow of the HTP. Each of these portal methods involves a flow of particle and vapor laden air and uses a concentration device that removes the target particles and vapor from the large volume of air by collecting them onto a mesh or substrate. The target particles and vapor are then thermally desorbed and mixed with a low volume flow of gas that leads to a chemical analyzer. Another portal method was disclosed by Bromberg et al in U.S. Pat. No. 5,760,314 and, which unlike the above non-contact portals, uses samplings tubes that make contact with individuals to efficiently collect particles and vapor.

A two-stage concentrator for vapor/particle detection was disclosed by Linker and Brusseau in U.S. Pat. No. 6,345,545. Their device enables concentrating particles from a high-volume gas flow to a sufficiently low-volume gas flow to be coupled efficiently to a detector. The first stage of the concentrator contains a metal mesh for collecting particles and vapor that are entrained in the high-volume gas flow. The desorbed vapors from the first-stage concentrator are collected on the second-stage concentrator and provided to the detectors with a low-volume gas flow.

The chemical detectors used in all of the portals mentioned above use some form of ETDs including ion mobility spectrometry (IMS), mass spectrometry (MS), and gas chromatography/chemiluminescence (GC/CL) detectors.

An important characteristic of a personnel screening portal is that it operate sufficiently fast so as not to significantly impede the flow of people going through it. Current portals operate with a sampling interval of about 10-15 s from one person to another. This is much longer than the interval of about 4-6 s for which standard metal detectors are capable. Methods to improve the sampling interval of a vapor/particle detecting portal are highly desirable.

Another important characteristic of a portal is that it have reasonable upfront and recurring costs per unit. Given the large number of passenger lanes in U.S. and international airports (about 3000 each) and limited available budgets, inevitable compromises are made with regard to cost and the number of units that can be deployed. Solutions that reduce the cost per passenger screened would allow greater distribution of deployed screening portals.

BRIEF SUMMARY OF THE INVENTION

A detector system that can analyze multiple samples with a single detector. The detector may contain a portal with a first opening and a second opening. A first sample is obtained from the first opening and a second sample is obtained from the second opening. The openings are coupled to a single detector that can analyze both samples. dr

BRIEF DESCRIPTION OF THE DRAWINGS

FIG. 8 is an illustration of an embodiment that has one concentrator, one blower, and four valves.

FIG. 9 is an illustration of embodiment that has one concentrator, one blower, and two valves.

DETAILED DESCRIPTION

Figure 1:
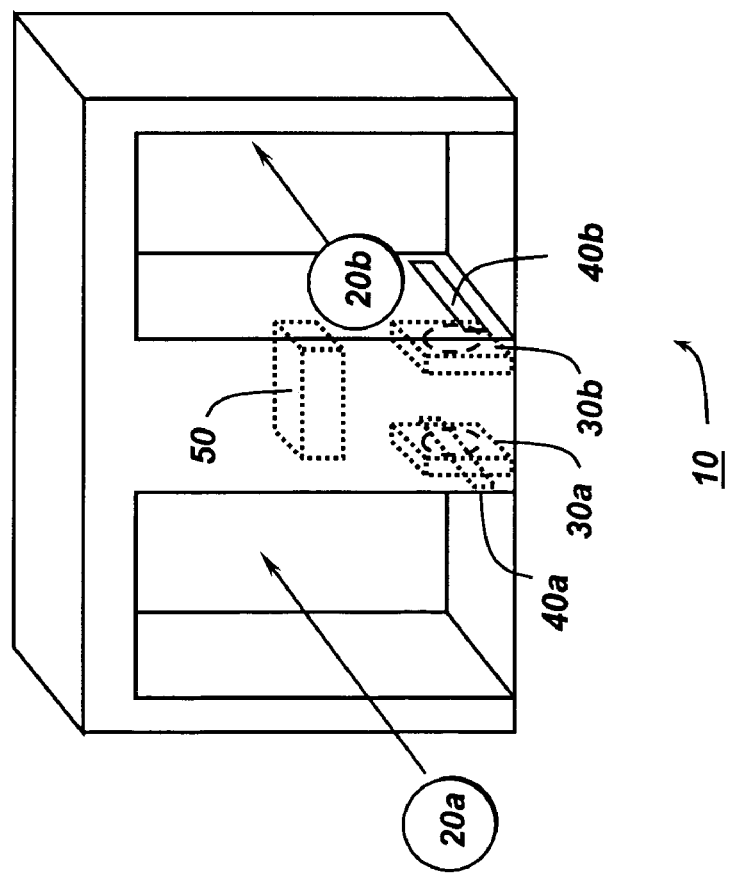
FIG. 1 is an illustration of a portal for screening two persons.

Disclosed is a personnel explosives-detecting portal capable of screening multiple persons at once or a combination of persons and baggage. Referring to the drawings more particularly by reference numbers, FIG. 1 shows an embodiment of a multiple trace portal detection system 10. The portal 10 allows two persons to be screened simultaneously. The portal has openings 20a and 20b. By way of example, the openings 20a and 20b may each be at least six feet high to allow people to pass through. Individuals do not have to enter at the same time. Each opening can operate independently.

The portal 10 may have two concentrators 30*a* and 30*b*. Vapor and particles of interest are collected off of individuals in openings 20*a* and 20*b* and are collected on concentrators 30*a* and 30*b*, respectively. The collection from both openings 20*a* and 20*b* can occur simultaneously or separately. The portal 10 may further have slots 40*a* and 40*b* that are in fluid communication with the openings 20*a* and 20*b* and allow vapor flow onto the concentrators 30*a* and 30*b*. Vapor and particles are pulled through the slots 40*a* and 40*b* and collected onto the concentrators 30*a* and 30*b*. The concentrators 30*a* and 30*b* then deliver the extracted vapor and particle content to a detector 50 by a heating process that leads to thermal desorption. The detector 50 may be of various types including mass spectrometry.

Though individuals may be screened simultaneously and collection of vapor and particles may occur simultaneously, the thermal desorption and detection process from the concentrators 30*a* and 30*b* may be conducted in sequence and not simultaneously in order to be able to differentiate which passageway is being analyzed. This sequence does not impede the ability to screen two passengers simultaneously because many steps are involved in the overall screening process. However, it is also feasible to thermally desorb from both concentrators simultaneously if differentiation of the analysis is not needed. This is reasonable since the probability of a positive detection for a target compound is low and having to do a follow-up screen on both individuals would not be unduly inconvenient.

Figure 2:
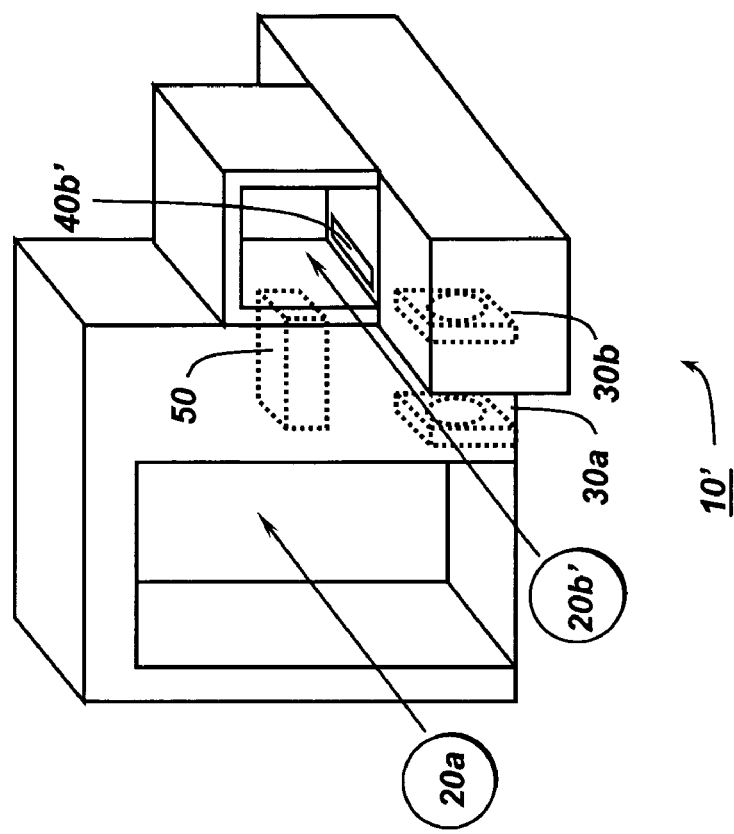
FIG. 2 is an illustration of a portal for screening a person and baggage.

FIG. 2 shows another embodiment of a portal 10' that can screen people and baggage. The opening 20*b*' of portal 10' is intended for screening baggage. By way of example, the opening 20*b* may be no greater than four feet high. The concentrator 30*b* is similar or the same as in the portal 10 shown in FIG. 1, and particle and vapor are drawn through slot 40*b*' similarly to slot 40*b*' in portal 10. Other types of screening may be used in combination with people or baggage including document screening, such as a boarding pass, or hand screening of people.

The multiple portal trace detection system may also contain other detection capabilities, such as a metal detector by prior art methods, in order to further improve the utilization with respect to maintaining high throughput for persons and baggage and to minimize floor space. The opening for people may also make use of doors to prevent people from passing through before an analysis has been conducted. A multiple portal configured for scanning baggage for targeted particle and vapor compounds may also include an x-ray detector to conduct internal screening by prior art methods.

Figure 3:
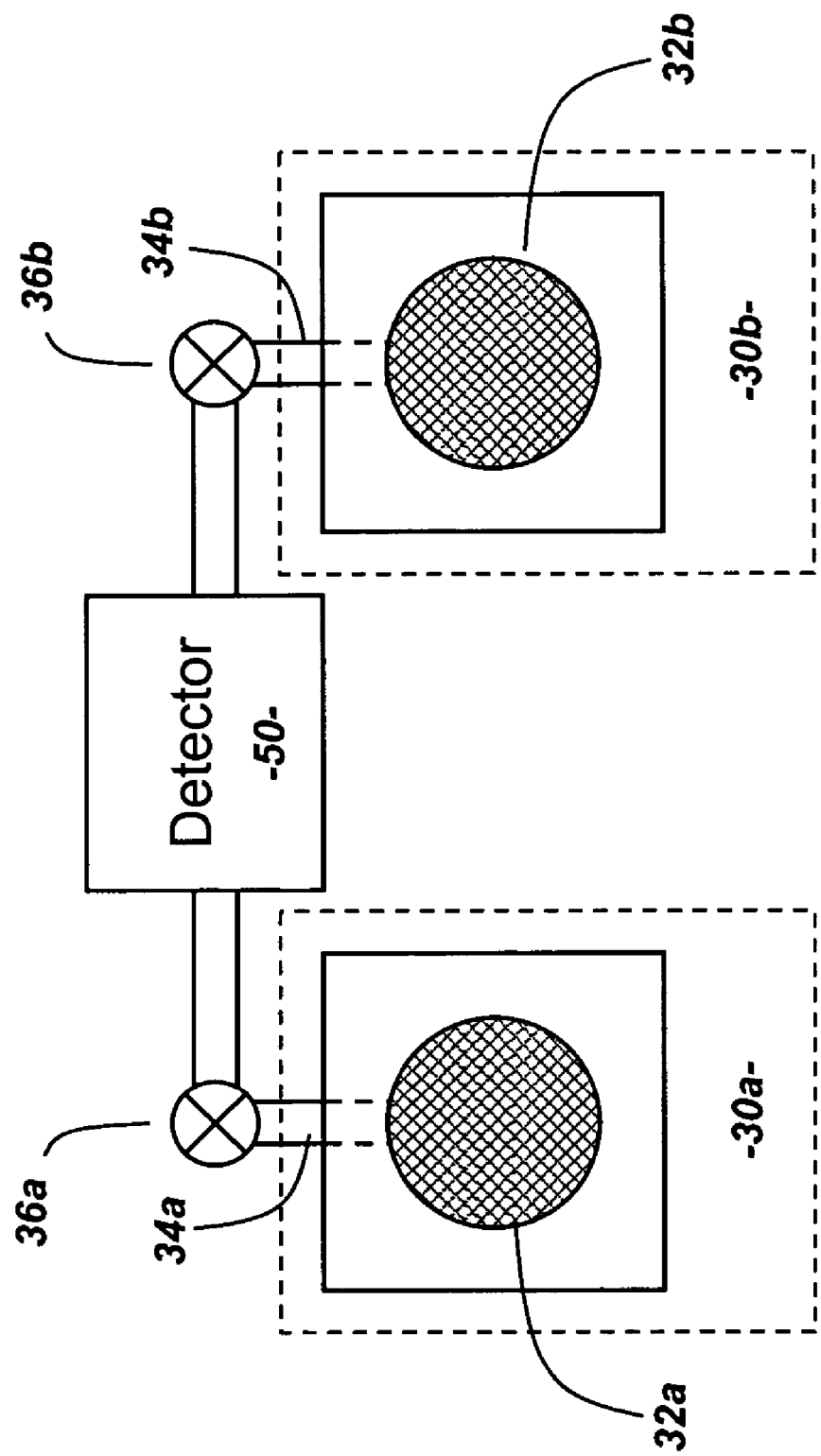
FIG. 3 is a schematic showing two particle/vapor concentrators coupled to a single detector by way of valves.

The embodiments shown in FIGS. 1 and 2 can be applied to a variety of concentrators and also to a variety of methods to collect target vapor and particles. FIG. 3 is an embodiment showing two concentrators 30*a* and 30*b* coupled to a single detector 50. The concentrators 30*a* and 30*b* may contain meshes 32*a* and 32*b*, respectively, that collect vapor and particles from air that is pulled through using a blower or pump. The portal may include valves 36*a* and 36*b* that are placed in the conduits 34*a* and 34*b*, respectively, and control fluid flow between the concentrators 30*a* and 30*b* and the detector 50. Because concentrators can hold vapor and particle content until a releasing event, such as thermal desorption by heating, it is also possible to operate without valves and use the heating event to deliver the vapor and particle content to the detector 50 as desired.

Figure 4:
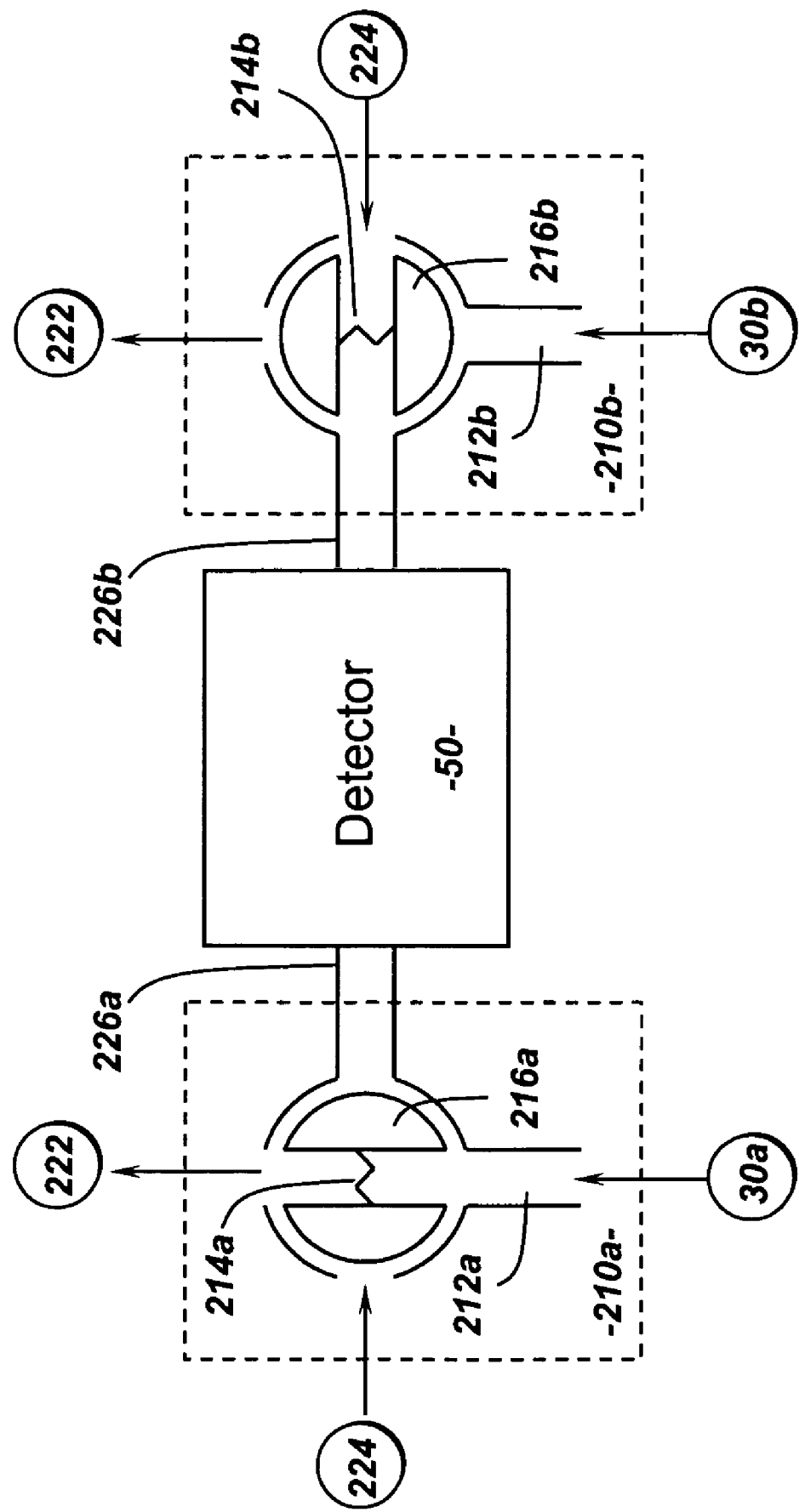
FIG. 4 is a schematic of a detector coupled to two second stage concentrators that are each coupled to a first stage concentrator.

FIG. 4 shows an embodiment that includes second-stage concentrators 21O*a* and 210*b*. The second-stage concentrators 210*a* and 210*b* may include channels 212*a* and 212*b* for passage of the desorbed vapor from the first-stage concentrators 30*a* and 30*b* to meshes or substrates 214*a* and 214*b* for collection of the desorbed vapor, and valves 216*a* and 216*b* for switching the path of the collected vapor from the first-stage concentrators 30*a* and 30*b* to the detector 50. The valve switching may be achieved by rotating the assembly as shown in FIG. 4. The collection phase is achieved using a pump 222 to force a fluid flow through the meshes 214*a* and 214*b* to capture particles and vapor. The delivery phase to the detector 50 is achieved using a pick-up flow from pump 224 to carry a desorbed vapor from the meshes 214*a* and 214*b* through channels 226*a* and 226*b* to the detector 50. The pump 224 may operate at a lower flow rate than pump 222. This allows for rapid collection with pump 222 and a flow rate more acceptable for conventional detectors 50 with pump 224.

The use of a second-stage preconcentrator coupled to a first-stage preconcentrator is a convenient means to control the switching of multiple concentrators to a single detector 50. It is possible for example for one concentrator 210*a* to be collecting vapor while the other concentrator 210*b* is delivering desorbed vapor to the detector 50 as illustrated in FIG. 4.

Figure 5:
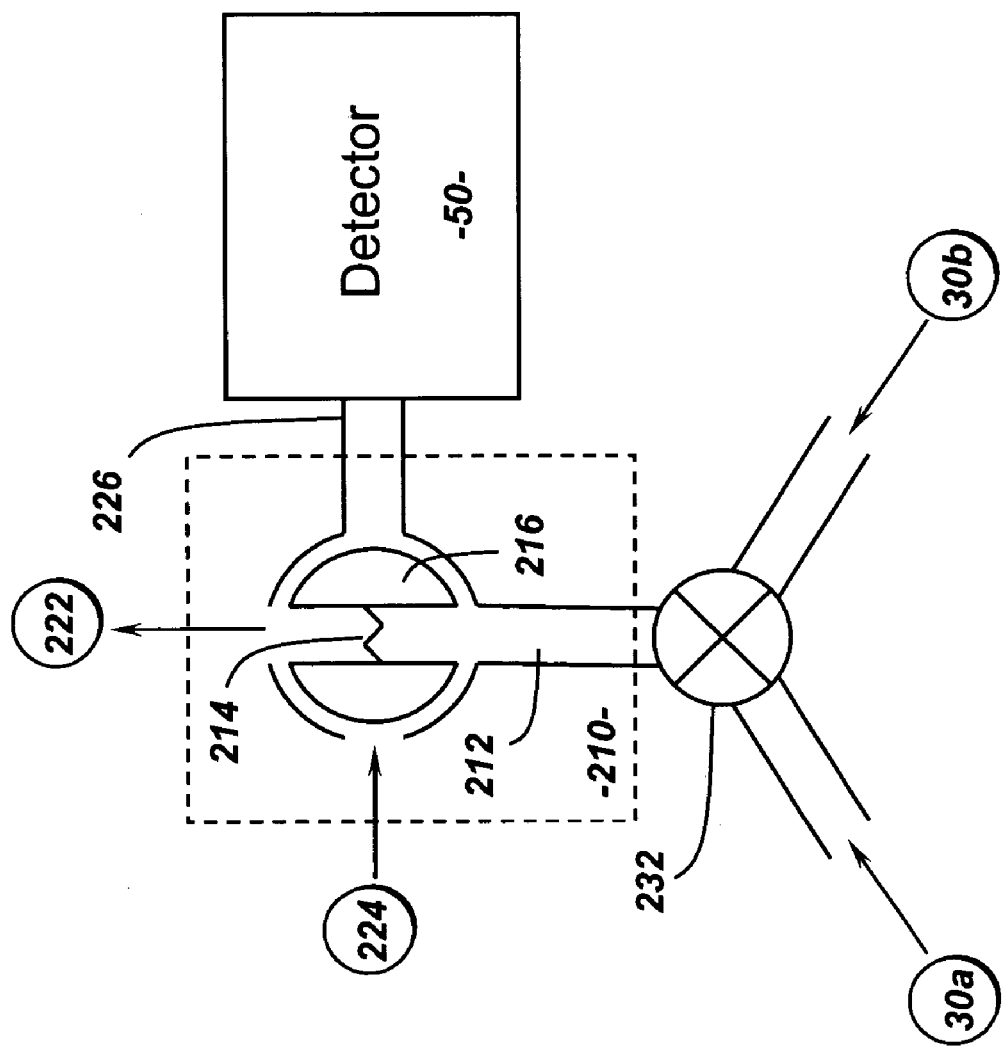
FIG. 5 is a schematic of a single-second stage concentrator and a detector that are coupled to two first-stage concentrators by way of a valve.

FIG. 5 shows another embodiment that includes a single valve 232 to switch the flow from the first-stage concentrators 30*a* and 30*b* to a single second stage concentrator 210. An advantage of this configuration is potential savings of cost and complexity by using only one second-stage preconcentrator.

Figure 6:
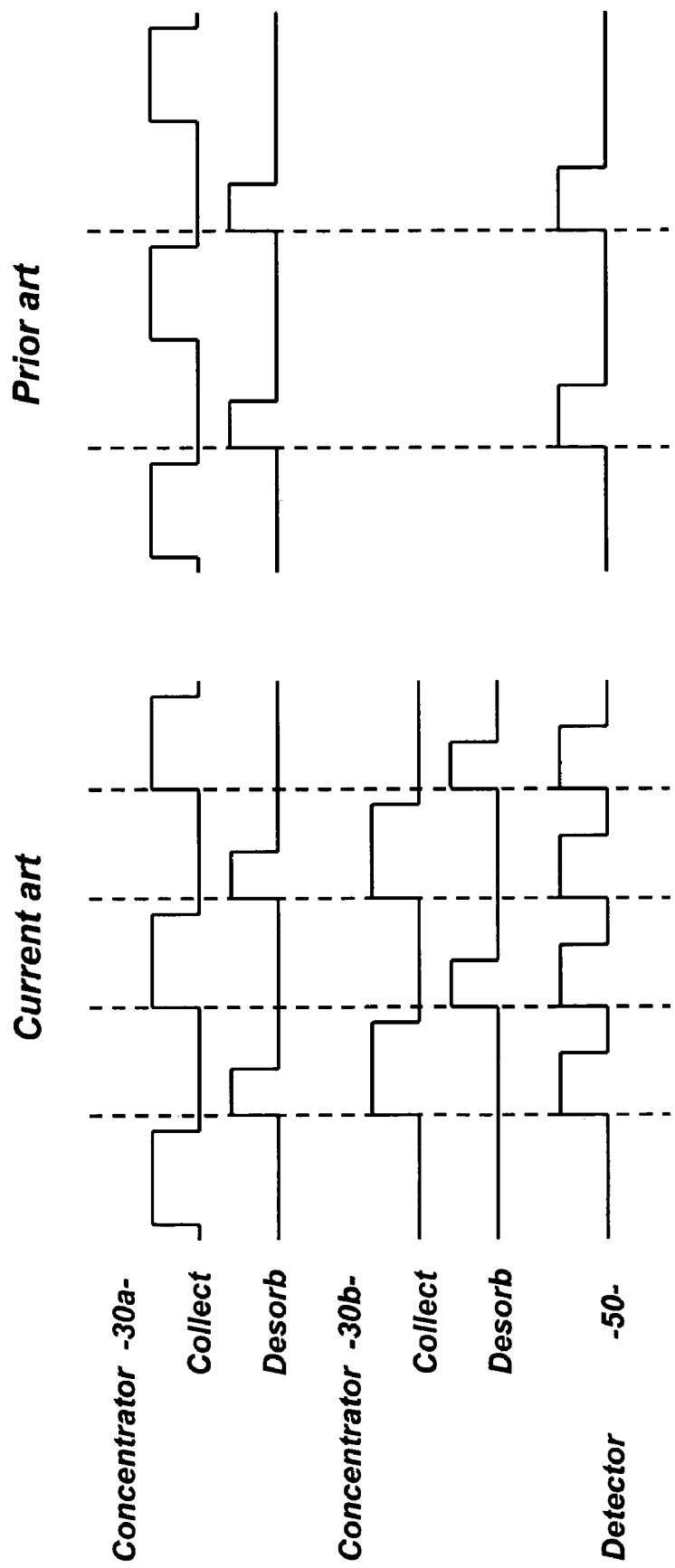
FIG. 6 is a timing diagram comparing a portal with two concentrators versus a portal with one concentrator.

FIG. 6 shows a timing diagram that illustrates the advantage of a multiple portal system with regard to increasing the speed and throughput of screening people and/or baggage. By way of example, FIG. 6 shows an example of a portal with a single-stage concentrator, but the timing diagram could also apply to a two- or more-staged concentrator. The concentrator 30 has two principal functions; to collect vapor and particles and to desorb them to the detector 50. The detector 50 operates during the desorb step as this is when the desorbed vapor enters the detector. Prior art portals use one opening 20, one concentrator assembly 30, and one detector 50. As shown in FIG. 6, the detector is required to operate only a fraction of the total screening cycle time.

A dual portal improves the utilization of the detector. For examples while concentrator 30*a* is desorbing and being analyzed by detector 50, concentrator 30*b* can be collecting sample. When 30*a* is done desorbing, 30*b* can then be switched to desorb with the detector analyzing that vapor stream, while concentrator 30*a* is now collecting. The dual portal is able to operate at twice the sampling rate while using only one detector. Depending on the concentrator collection time versus the concentrator desorb and detector analysis time, it is possible to increase the number of portal openings to more than two. For example, if the collection time was 8 sec and the desorb and analysis time was 2 sec, then it is possible to have five openings and achieve up to five times the throughput with the single detector. Some dead time between switching may partially reduce the effective sampling rate.

Figure 7:
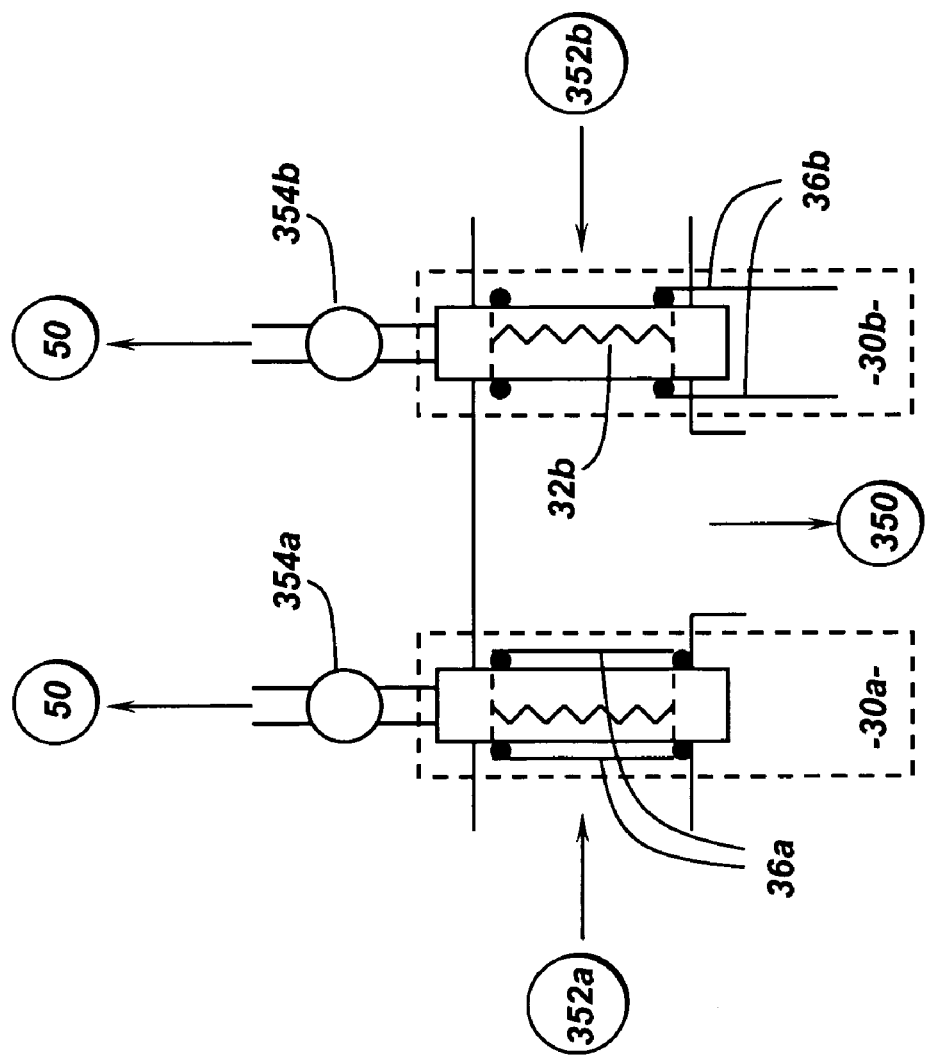
FIG. 7 is an illustration showing an embodiment with two concentrators and one airflow blower.
Figure 10B:
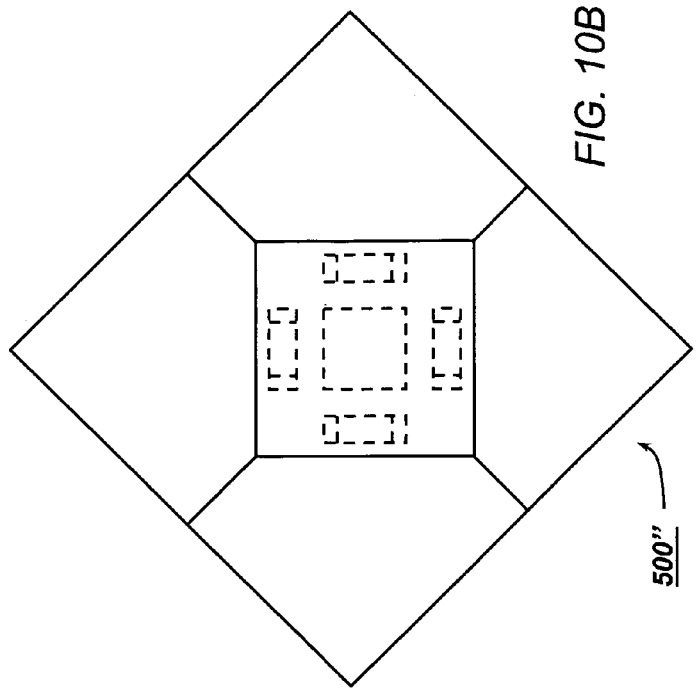
FIGS. 10A-D are illustrations of embodiments of a portal with a single detector that can screen more than two persons.
Figure 10D:
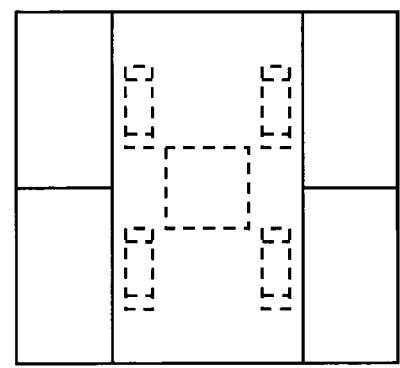
Figure 10A:
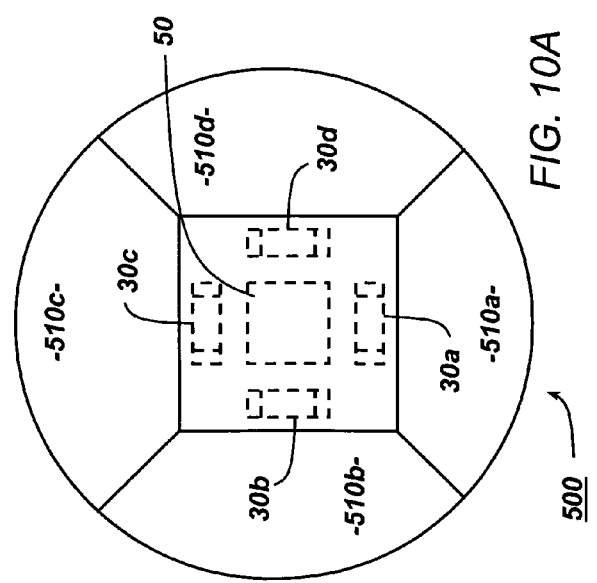
Figure 10C:
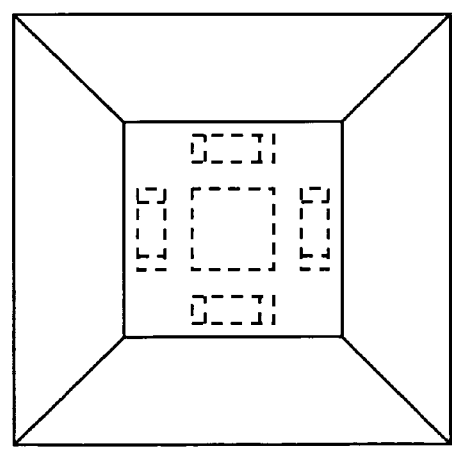

It is also advantageous for a multi-opening portal to share other components besides the detector 50. FIG. 7 shows another embodiment that uses a single pumping system or blower 350 to pull a large-volume flow from portal openings 352*a* and 352*b* through the concentrators 30*a* and 30*b*. One means to switch the flow from one or the other concentrator is to use valves 36*a* and 36*b* to isolate the concentrators 30 from the large-volume flow. The valves may be a sliding gate valve, a hinged butterfly valve, or a shutter-iris type valve, for example. Other valve methods may also be used. This embodiment may have components 354a and 354b that control the flow of samples to the detector 50.

The components 354a and 354a can be either valves, such as 36 in FIG. 3, or second-stage concentrators, such as 210 in FIG. 4. It is also possible to have a combination of valve and second-stage concentrator 210 as illustrated in FIG. 5.

FIG. 8 shows another embodiment of a multi-opening portal that uses a single concentrator 30, a single blower 350, second-stage concentrator or valve 354, and a single detector 50. This embodiment may have four valves 400a, 402a, 400b and 402b that can control fluid flow through openings 352a or 352b and across the concentrator 30. FIG. 9 shows another embodiment that utilizes only two valves 410a and 410b to control flow through the openings 352a and 352b and across the concentrator 30. The type of valve shown is general and can be a gate valve, butterfly valve, iris or shutter, or other means.

Although dual port portals have been shown, and described, it is possible to perform sampling with more than two openings and a single detector. FIG. 10A-D show various configurations 500, $_{500}$', 500", and 500'" of four sampling openings 510a-d that are coupled to concentrators 30a-d. The concentrators 30a-d are coupled to the same detector 50. The entry and exit points may be the same doorway or two doorways.

While certain exemplary embodiments have been described and shown in the accompanying drawings, it is to be understood that such embodiments are merely illustrative of and not restrictive on the broad invention, and that this invention not be limited to the specific constructions and arrangements shown and described, since various other modifications may occur to those ordinarily skilled in the art.

What is claimed is:

1. A detector system, comprising:
   a portal that has a first opening and a second opening;
   a first concentrator that is coupled to said first opening;
   a second concentrator that is coupled to said second opening;
   a single detector coupled to said first and second concentrators; and,
   a pump coupled to said first and second openings so that said first concentrator collects vapor and particles through said first opening and said second concentrator collects vapor and particles through said second opening, simultaneously with said first concentrator collecting vapor and particles.

2. The system of claim 1, wherein said portal includes a first slot that contains said first concentrator and a second slot that contains said second concentrator.

3. The system of claim 1, wherein said first and second openings each have a height of at least six feet.

4. The system of claim 1, wherein said first opening has a height of at least six feet and said second opening has a height no greater than four feet.

5. The system of claim 1, further comprising a first valve coupled to said first concentrator and said detector.

6. The system of claim 1, further comprising a second stage concentrator coupled to said first and second concentrators and said detector.

7. The system of claim 1, further comprising a pair of second stage concentrators coupled to said first and second concentrators and said detector.

8. The system of claim 1, wherein said detector includes a mass spectrometer.

9. A method for analyzing samples, comprising:
   obtaining a first sample from the first opening of a portal; and,
   obtaining a second sample from a second opening of the portal, simultaneously with obtaining the first sample from a first opening; and, analyzing the first sample with a single detector.

10. The method of claim 9, wherein the first and second samples are analyzed sequentially by the single detector.

11. The method of claim 9, wherein the first sample is obtained by a first concentrator and the second sample is obtained by a second concentrator.

12. The method of claim 9, wherein the first and second samples are obtained by a single concentrator.

13. The method of claim 12, wherein the first and second samples are pulled through the concentrator with a pump.

* * * * *